(12) United States Patent
Wilcox et al.

(10) Patent No.: US 7,618,424 B2
(45) Date of Patent: Nov. 17, 2009

(54) ORTHOPEDIC INSTRUMENT

(75) Inventors: Bryan S. Wilcox, Collierville, TN (US); Rodney Ballard, Lakeland, TN (US); Chris E. Johnson, Germantown, TN (US); George Frey, Englewood, CO (US)

(73) Assignee: Warsaw Orthopedic, Inc.

( * ) Notice: Subject to any disclaimer, the term of this patent is extended or adjusted under 35 U.S.C. 154(b) by 342 days.

(21) Appl. No.: 11/118,513

(22) Filed: Apr. 29, 2005

(65) Prior Publication Data
US 2006/0247645 A1 Nov. 2, 2006

(51) Int. Cl.
*A61B 17/58* (2006.01)
*A61B 17/60* (2006.01)
*A61F 2/00* (2006.01)

(52) U.S. Cl. .................... 606/105; 606/86 R; 606/96
(58) Field of Classification Search .............. 606/61, 606/69, 86, 96, 99, 101, 104, 105, 246–279; 600/213, 217, 227, 230, 23; 403/13, 14, 403/254, 19, 20, 49, 297, 294, 292, 293, 403/354
See application file for complete search history.

(56) References Cited

U.S. PATENT DOCUMENTS

| 2,779,966 | A | * | 2/1957 | Torchia | 16/244 |
| 4,585,247 | A | * | 4/1986 | Takada | 280/281.1 |
| 4,957,495 | A | * | 9/1990 | Kluger | 606/58 |
| 5,005,562 | A | | 4/1991 | Cotrel | |
| 5,795,291 | A | * | 8/1998 | Koros et al. | 600/232 |
| 5,797,911 | A | | 8/1998 | Sherman et al. | |
| 6,648,891 | B2 | * | 11/2003 | Kim | 606/69 |
| 7,083,621 | B2 | * | 8/2006 | Shaolian et al. | 606/61 |
| 2003/0105471 | A1 | * | 6/2003 | Schlapfer et al. | 606/104 |
| 2004/0210232 | A1 | * | 10/2004 | Patel et al. | 606/96 |
| 2005/0021040 | A1 | * | 1/2005 | Bertagnoli | 606/90 |
| 2005/0203532 | A1 | * | 9/2005 | Ferguson et al. | 606/90 |
| 2006/0052671 | A1 | * | 3/2006 | McCarthy | 600/232 |
| 2006/0247649 | A1 | | 11/2006 | Rezach et al. | |

FOREIGN PATENT DOCUMENTS

| FR | 2 821 543 | 9/2002 |
| WO | WO 2003/065900 | 8/2003 |
| WO | WO 2004/041100 | 5/2004 |
| WO | WO 2005/009209 | 2/2005 |
| WO | WO 2005/018490 | 3/2005 |

\* cited by examiner

*Primary Examiner*—Thomas C Barrett
*Assistant Examiner*—Andrew Yang

(57) ABSTRACT

An apparatus for use in orthopedic distraction or compression is disclosed. In the illustrated embodiments, two arms are provided that are connected by a rod or bar with a mechanism that enables the arms to be brought toward or away from each other. At the end of each arm, a tip for connecting to a bone implant is provided. The tips are pivotable with respect to the arms, and have an opening with a tab that allows insertion of an implant head having branches defining a channel. Once the tips are appropriately positioned, connected and locked to the bone implants, the mechanism can be operated to move the arms together in compression or apart in distraction.

45 Claims, 7 Drawing Sheets

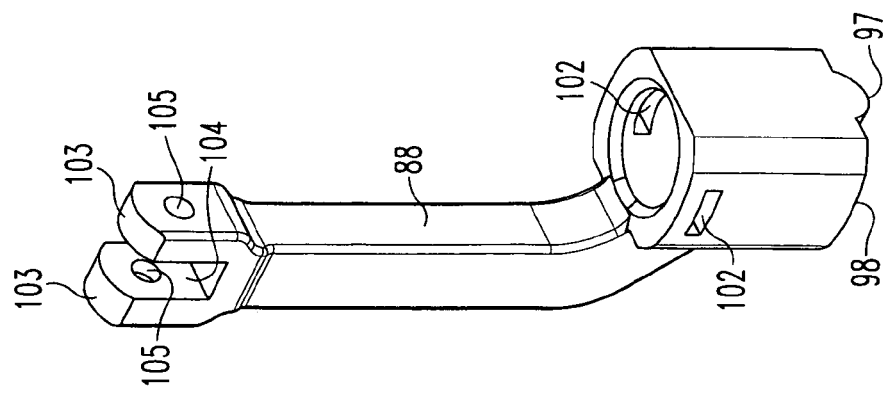
*Fig. 7*
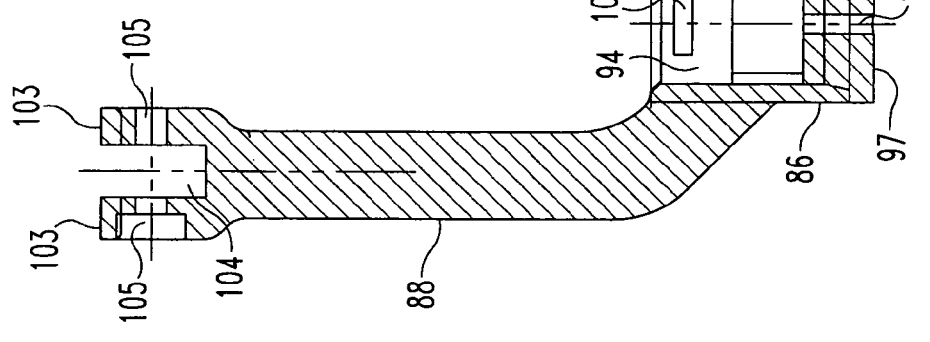
*Fig. 5*
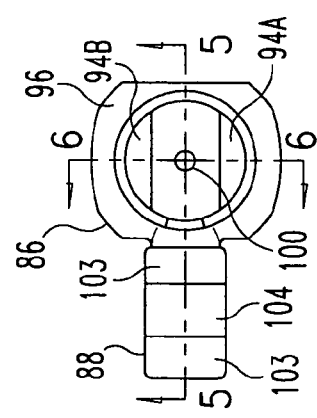
*Fig. 4*
*Fig. 6*

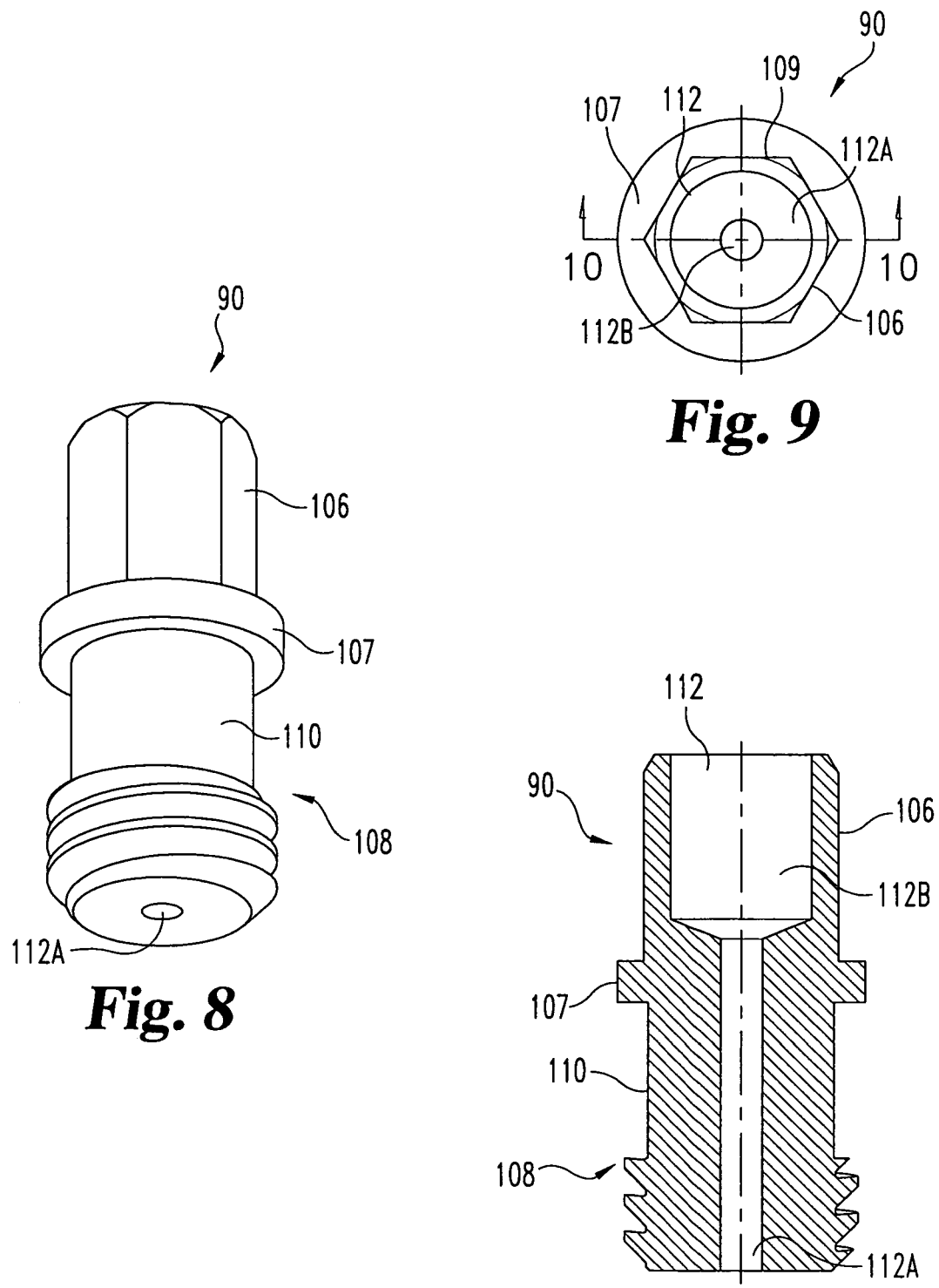

ORTHOPEDIC INSTRUMENT

The present disclosure relates to instrumentation useful in orthopedic surgery, and in particular to instrumentation useful in manipulating (e.g. distracting or moving apart) tissues such as bones (e.g. vertebrae) or bone fragments.

BACKGROUND

Several types of tools for compressing or distracting tissues such as bones or bone fragments toward healing of a trauma or correcting of an abnormality are known. Among these include instruments that use cables to pull together bones or artificial implants placed in such bones, scissor-like tools that apply leverage around a central fulcrum to move bones or implants toward or away from each other, and even the surgeon's own hands. Such manipulations or adjustments of bones are indicated for correction of a number of orthopedic conditions. For example, in the case of a scoliosis or other abnormal positioning of the spine, one or more vertebrae or vertebral segments may require compression or distraction with respect to adjacent bones to achieve a better or more normal position. In the case of a trauma, for example after an injury to a bone or adjacent tissue or removal of a cancerous or other mass, compression or distraction of tissue may be required to induce proper healing, to accommodate a therapy such as implantation of spacing or holding devices or of therapeutic material (e.g. bone morphogenic protein (BMP), allograft, autograft or other osteogenic substances, or medications), or for other reasons. Prior compression and/or distraction tools are not always useful, or may be awkward to use, in certain surgical pathologies or situations. Thus, there remains a need in the art for such instruments that provide advantages over existing tools.

BRIEF DESCRIPTION OF THE DRAWINGS

FIG. 4 is a top view of part of the structure shown in FIG. 3.

FIG. 5 is a cross-sectional view of the structure shown in FIG. 4, taken along the lines 5-5 in FIG. 4 and viewed in the direction of the arrows.

FIG. 6 is a cross-sectional view of the structure shown in FIG. 4, taken along the lines 6-6 in FIG. 4 and viewed in the direction of the arrows.

FIG. 7 is a perspective of the structure shown in FIGS. 4-6.

FIG. 8 is a perspective view of an embodiment of another aspect of the embodiment shown in FIG. 1.

FIG. 9 is a top view of the structure shown in FIG. 8.

FIG. 10 is a cross-sectional view of the structure shown in FIG. 9, taken along the lines 10-10 in FIG. 9 and viewed in the direction of the arrows.

DESCRIPTION OF THE ILLUSTRATED EMBODIMENTS

Figure 1:
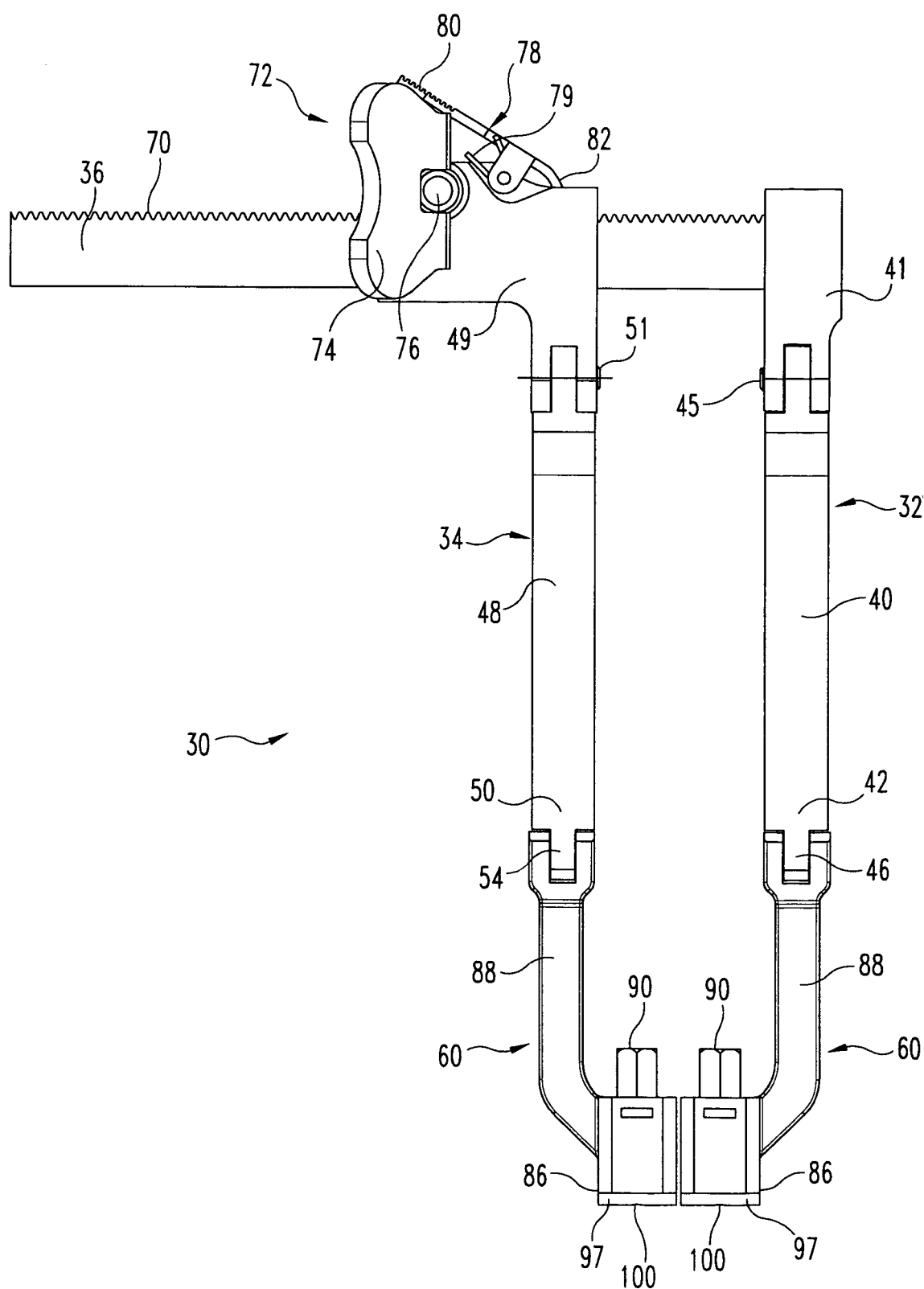
FIG. 1 is a front view of an embodiment of an instrument useful in orthopedic surgery.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated, as would normally occur to one skilled in the art to which the invention relates.

An embodiment of an instrument 30 is shown in FIG. 1. Instrument 30 has arms 32 and 34 connected by a toothed rod, bar or rack 36. Arm 32, in an illustrated embodiment, is substantially rectangular in cross-section along a medial portion 40, and has a first end 41 that connects to rod 36, and a second end 42. In some embodiments, end 41 is pivotably connected to medial portion 40 by an axle 45, which may be a screw or other threaded element. In other embodiments, end 41 may be fixed to or integral with medial portion 40 so that end 41 and medial portion 40 cannot pivot with respect to each other. End 41 is fixed with respect to rod 36 in a particular embodiment, as by gluing, welding, interference fitting or otherwise. Second end 42 includes a tongue 46 with a hole 47 for accommodating an axle. Tongue 46 may connect to an assembly such as assembly 60 via an axle so that assembly 60 is pivotable with respect to arm 32.

Arm 34 has a medial portion 48 connected to a first end 49 and a second end 50. An illustrated embodiment of end 49 is substantially L-shaped and is pivotably connected to medial portion 48 by an axle 51, which could be substantially identical to axle 45. In other embodiments, end 49 may be fixed to or integral with medial portion 48 so that end 49 and medial portion 48 cannot pivot with respect to each other. End 49 has a channel 52 in which rod 36 sits, and is movable with respect to rod 36, as will be further discussed below. Second end 50 includes a tongue 54 with a hole 56 for accommodating an axle. Tongue 54 may connect to an assembly such as assembly 60 via an axle so that assembly 60 is pivotable with respect to arm 34.

Rod 36 is shown in one embodiment as a flattened substantially rectangular solid. It will be understood that bar 36 could have any of a number of shapes, such as an elongated solid with a cross-section in the shape of a circle, square, triangle or other polygon. The illustrated embodiment of bar 36 includes a set of teeth or ridges 70 along one side, e.g. a top side.

In a specific embodiment a pinion mechanism 72 extends through a part of end 49 and into channel 52. Pinion mechanism 72, in one embodiment, has a handle 74 pivotably connected to a pinion 76, which has teeth or ridges in channel 52 and in contact with teeth 70 or rod 36 in rack-and-pinion fashion, so that turning pinion mechanism 72 results in linear movement of arm 34 with respect to rod 36. A locking pawl 78 may be included. In one embodiment, pawl 78 is a lever biased by spring 79 and attached to end 49, having a pushing surface 80 and a tooth-engaging end 82. Pushing on pushing surface 80 rotates pawl 78 to disengage tooth-engaging end 82 from teeth 70 of rod 36, permitting free movement of arm 34 with respect to rod 36. Releasing pushing surface 80 allows tooth-engaging end 82 to resume its spring-biased position engaging teeth 70. In embodiments having rod 36, arms 32 and 34, and pinion mechanism 72 and pawl 78 if included, are pre-assembled prior to surgery to form essentially a single "rack" unit for the surgeon's use.

In the illustrated embodiment, pawl 78 is oriented to allow distraction while pawl 78 is in its spring-biased state (i.e. when tooth-engaging end 82 engages teeth 70), while limiting or preventing compression. To enable compression of bone tissue such as vertebrae, i.e. moving bones or bone pieces generally toward each other, pawl 78 may be disengaged from teeth 70 in the illustrated embodiment, or may be oriented 180 degrees opposite to what is shown in the illustrated embodiment, or may be left out altogether.

Assemblies 60 can hold implants, for example implants having a U-shaped channel in them for accommodating a rod, bar, plate or other support. Such implants may include those disclosed in U.S. Pat. No. 5,005,562 to Cotrel, U.S. Pat. No. 5,797,911 to Sherman, both of which are incorporated by reference herein in their entireties, or other bone screws, hooks, clamps or other implants having an open back forming a channel.

In an illustrated embodiment, assemblies 60 include a tip 86, a leg 88, a set screw 90, and one or more stakes 92. Tip 86, in an illustrated embodiment, is slightly offset with respect to leg 88, making assembly 60 substantially J-shaped. Tip 86 may be substantially rectangular with rounded corners in cross-section, or may be substantially cylindrical or have any of a variety of cross-sectional shapes. An opening 94 extends through a top surface 96 of tip 86, and in a particular embodiment opening 94 is substantially parallel to the arm 32, 34 to which assembly 60 is connected. Opening 94 is divided into openings 94A and 94B in the illustrated embodiment by a tab or protrusion 97 along bottom surface 98 of tip 86. Tab 97 is part cylindrical in one embodiment, and may be of a size approximately the same as a channel through an orthopedic implant. An aperture 100 through bottom surface 98 communicates with opening 94. Aperture 100 and opening 94 could be thought of as one opening. In a particular embodiment, aperture 100 is of a size to allow passage of a guide wire through aperture 100 and opening 94. One or more side openings 102 may also be provided in tip 86, and may communicate with opening 94. Opening(s) 102 are substantially flat or rectangular in the illustrated embodiment to accommodate stakes 92. Openings 102 may be of any appropriate shape that will accommodate stakes 92.

Leg 88 joins to tip 86 at one end, and leg 88 and tip 86 may be integral or otherwise fixed to each other. At an opposite end, prongs 103 with a slot 104 between them are found in the illustrated embodiment. Slot 104 is sized to accommodate tongue 46 of arm 32. Prongs 103 each have holes 105 for accommodating an axle (not shown), and holes 105 may align with hole 47 through tongue 46 when tongue 46 is in slot 104. In embodiments in which one or both holes 105 are threaded, the axle through holes 105 and hole 47 may be a screw. Connections between leg 88 and arm 34 are substantially the same.

The illustrated embodiment of set screw 90 has a head portion 106, a collar 107, and an at least partially threaded shaft 108. Head portion 106 may have an external print 109, such as a hexagonal print, or an internal print for accommodating a driving tool. Collar 107 is of a diameter at least slightly less than the diameter of opening 94. The threads on shaft 108 are configured to be compatible with internal threads on an implant. A portion 110 of shaft 108 is not threaded in an illustrated embodiment. In a particular embodiment, set screw 90 may be cannulated, with an opening 112 having a portion 112A that is sized to accommodate a guide wire, and a portion 112B that is larger in diameter than portion 112A and has a conical surface adjoining portion 112A to aid one in placing a guide wire through set screw 90.

Stakes 92 are substantially flat rectangular disks with a concave surface 114 in the illustrated embodiment. Stakes 92 are inserted into openings 102 so that concave surface 114 extend into opening 94 of tip 86, and are fixed therein as by gluing, welding, interference fitting (e.g. inserting a cold or otherwise contracted stake 92 into opening 102 and allowing it to expand), or otherwise. Concave surfaces 114 form part of a cylinder in the illustrated embodiment. Stakes 92 are inserted so that the distance between their respective concave surfaces 114 through the axis of opening 102 is at least slightly greater than the diameter of shaft portion 110, and is at least slightly smaller than the diameter of collar 107. In a particular embodiment, the crest diameter of the threads on shaft 108 is at least slightly greater than the distance between the respective concave surfaces 114 of stakes 92 through the axis of opening 102. Stakes 92 retain set screw 90 within opening 94.

Use of an embodiment of instrument 30 will now be described with reference to a surgical procedure on the spine using bone screws such as those shown in U.S. Pat. No. 5,005,562 or U.S. Pat. No. 5,797,911, which have a head with two branches forming a U-shaped channel that is internally threaded, as an example. As noted above, instrument 30 may be used in a variety of orthopedic treatments, at other surgical sites, and/or with other types of implants.

To treat the condition or injury of the patient, the surgeon obtains access to the surgical site in a manner well known in the art, e.g. through incision and refraction of tissues. Once access to the surgical site has been obtained, e.g. via an opening such as a midline incision above the affected area, with tissue being resected laterally to the transverse process, or by other surgical procedure. The surgeon may connect one or more screws to adjacent or nearby vertebrae that require compression or distraction in order to relieve or improve their condition. For example, pilot holes in vertebrae, e.g. in pedicles, may be made, and screws may be inserted into or otherwise connected to two or more vertebrae. In one embodiment, a support member (for example, a spinal rod, with or without appropriate lateral or other connectors) may be connected to the screws, as by placing or reducing it into the channels in the screws, and tightening to one of the screws.

Once such implants are placed as desired by the surgeon, the surgeon can move instrument 30 into position adjacent the implants. The surgeon may first adjust the distance between arms 32 and 34 to approximately the distance between the inserted bone screws. In an embodiment in which aperture 100 is provided, and in which cannulated implants have been placed with the assistance of a guide wire, the guide wire can be inserted through aperture 100 and opening 94 of tip 86, and tip 86 can be moved along the guide wire until it is adjacent or abutting the implant. Referring again for convenience to an implanted screw S, the screw head and/or tip 86 is maneuvered so that branches B of screw S at least partially enter openings 94A and 94B through bottom surface 98 of tip 86. In one embodiment, branches B are advanced into tip 86 so that tab 97 is within the channel between branches B, and in a particular embodiment branches B are advanced so that tab 97 is adjacent to or abutting a floor of the channel between branches B.

Set screw 90 is then turned so as to thread its shaft 110 into the threaded channel of the bone screw S. Set screw 90 may be turned as desired by the surgeon. If it is turned relatively little, it may simply engage the threads in the bone screw channel to hold the bone screw in tip 86. If set screw 90 is tightened substantially, then it will draw bone screw S further into tip 86 until tab 97 abuts the floor of the channel of the bone screw or a support member within the channel. In the latter case, the bone screw head is securely fixed with respect to tip 86. The head of the bone screw is held from turning with set screw 90 by the tab 97 within the bone screw channel. With tightening of set screw 90 so that tab 97 is forced against the bone screw or other implant head, the screw S may be locked so that the branches and implant head are substantially inhibited from motion relative to each other or to tip 86. Such locking may be analogous to the locking that occurs when a set screw is tightened against a rod within a screw S, such as is also disclosed in U.S. Pat. No. 5,797,911.

When each of assemblies 60 is connected or locked to a respective bone screw head, compression or distraction of the bones to which the bone screws are attached can occur. Operating pinion mechanism 72, e.g. by turning handle 74, to move arms 32 and 34 away from or toward each other accomplishes distraction or compression. For example, in the embodiment shown in FIG. 1, turning handle 74 counterclockwise will force arm 34 along rod 36 away from arm 32 and distract bones connected to arms 32 and 34 via assemblies 60. Turning handle 74 clockwise (assuming modifications to or release of pawl 78, as disclosed above, have taken place) will force arm 34 toward arm 32 to compress bones connected to arms 32 and 34. Once a satisfactory distraction or compression has been achieved, set screws 90 for each assembly 60 may be unscrewed from the channels of their respective bone screws, allowing assemblies 60 and the rest of the instrument to be pulled away from the bone implants and away from the surgical site. In embodiments in which set screw 90 can be removed from tip 86 (i.e. stakes 92 do not interfere with shaft 110 of set screw 90), a locking screw can be placed through opening 94 and into the head of bone screw S to lock it. If a guide wire is used, set screw 90 may be removed along the guide wire, and a cannulated locking screw can be inserted along the guide wire. The surgeon can complete the locking of the implants and support(s), and otherwise complete the surgical procedure.

Figure 11:
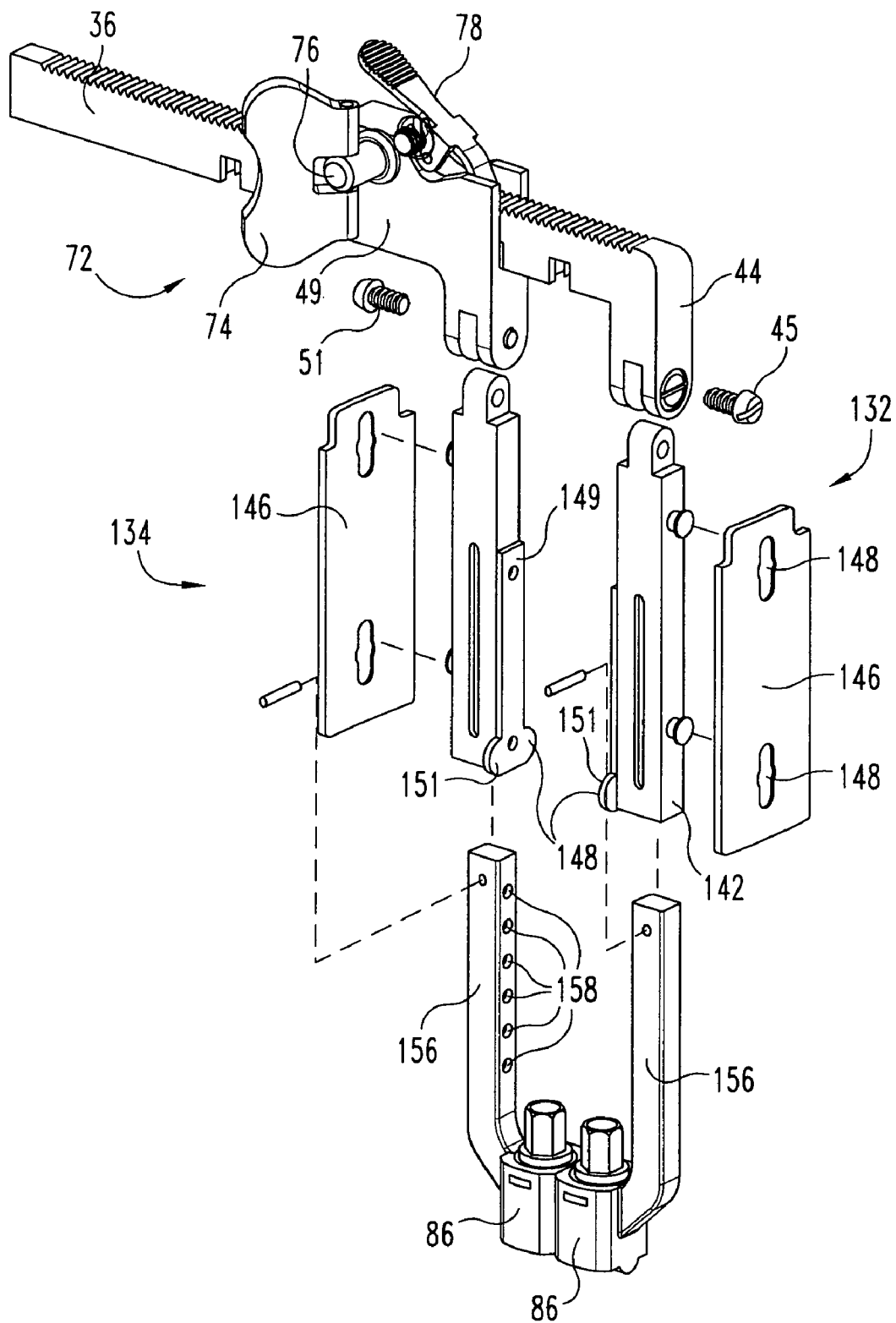
FIG. 11 is an exploded view in perspective of an embodiment of an instrument useful in orthopedic surgery.
Figure 12:
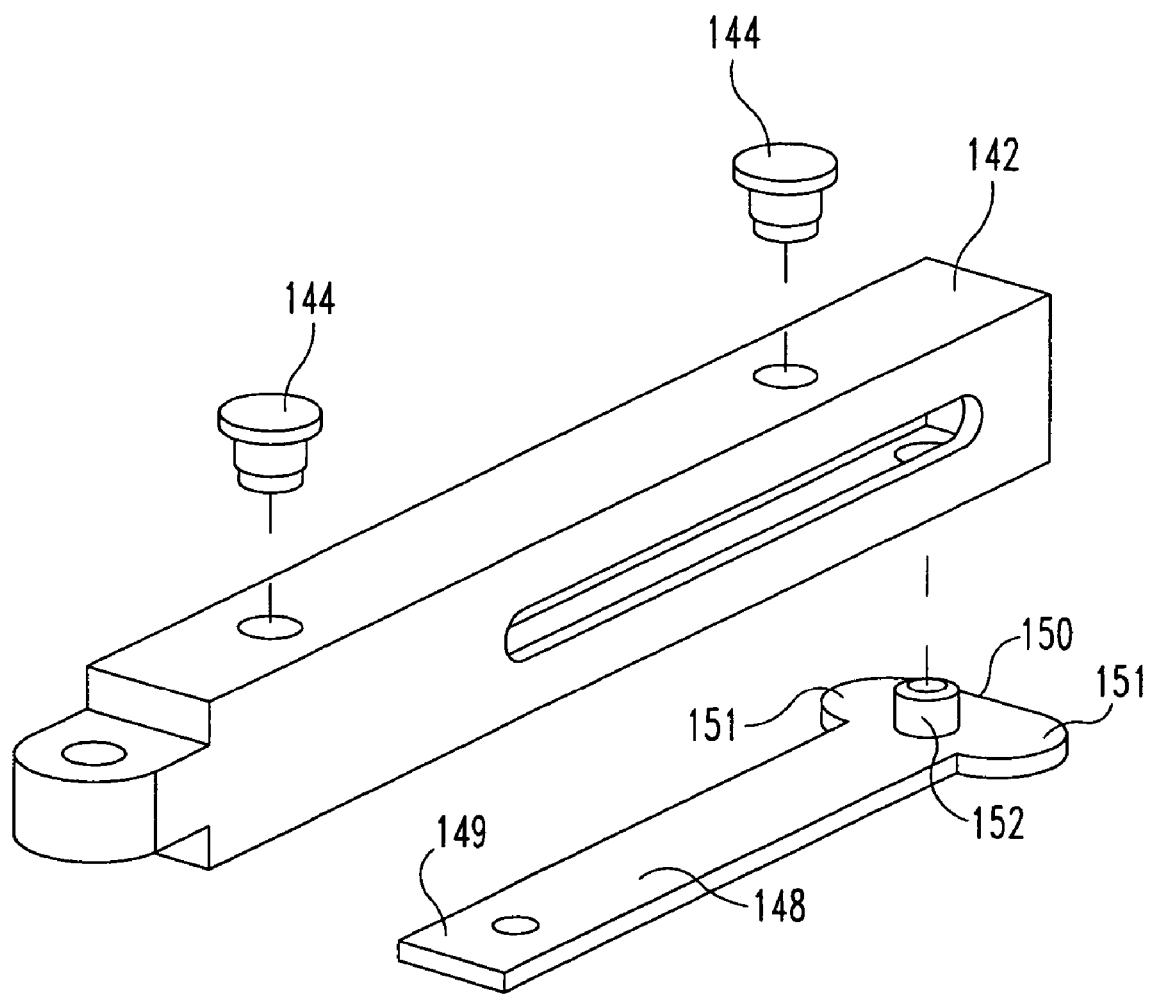
FIG. 12 is an exploded view in perspective of an aspect of the embodiment shown in FIG. 11.

Referring generally to FIG. 11, there is shown another embodiment of arms 132 and 134 that may be used with instrument 30. Arms 132 and 134 are different from arms 32 and 34 principally in that arm 132 is made integral with rod 36 and in the ways discussed below, and are otherwise substantially the same as arms 32 and 34. Other aspects of the embodiment of instrument 30 shown in FIG. 1 are substantially similar or identical to the embodiment shown in FIG. 11.

For simplicity, features of arm 132 will be described, it being understood that similar or identical features are found in arm 134. The illustrated embodiment of arm 132 includes a medial portion 142 that is hollow through a lower portion and substantially square or rectangular. On one side of medial portion 142, in one particular embodiment the side not facing the other arm 134, two flanged protrusions 144 are provided that connect with a retractor blade 146 via oblong holes 148 that are larger at a middle portion (e.g. slightly larger than the flange of protrusions 144) than at end portions. Retractor blade 146 assists in holding or moving tissue out of the way when arm 132 is at the surgical site and/or in the midst of distraction or compression procedure. On an opposite side of medial portion 142 a locking arm 148 is attached. An upper end 149 of locking arm 148 is attached to medial portion 142, as by a pin or by welding, gluing or other fixing methods, so that locking arm is effectively biased into a close juxtaposition with medial portion 142. A lower end 150 of locking arm 148 includes side tabs 151 and a protrusion 152. Protrusion 152 extends through a hole and into the hollow interior of medial portion 142.

In this embodiment, a leg 156 connected to tip 86 is configured to fit within medial portion 142 in a telescoping manner. Leg 156 includes a series of holes 158 along its length. Holes 158 may be spaced uniformly along the length of leg 156. Holes 158 are on a side of leg 156 that will face protrusion 152 of locking arm 148 when leg 156 is inserted into medial portion 142, and are sized so that protrusion 152 can fit inside them. Leg 156 is thus adjustable with respect to medial portion 142, so that the overall length from rod 36 to tip 86 is variable. Pulling one or both side tabs 151 or another part of locking arm 148 removes protrusion 152 from within medial portion 142. Leg 156 can then be moved within medial portion 142 to a desired relative position, and locking arm 148 is released. Locking arm 148 returns to its unstressed condition, and protrusion 152 enters medial portion 142 and one of holes 158, holding leg 156 in a desired position relative to medial portion 142.

Figure 2:
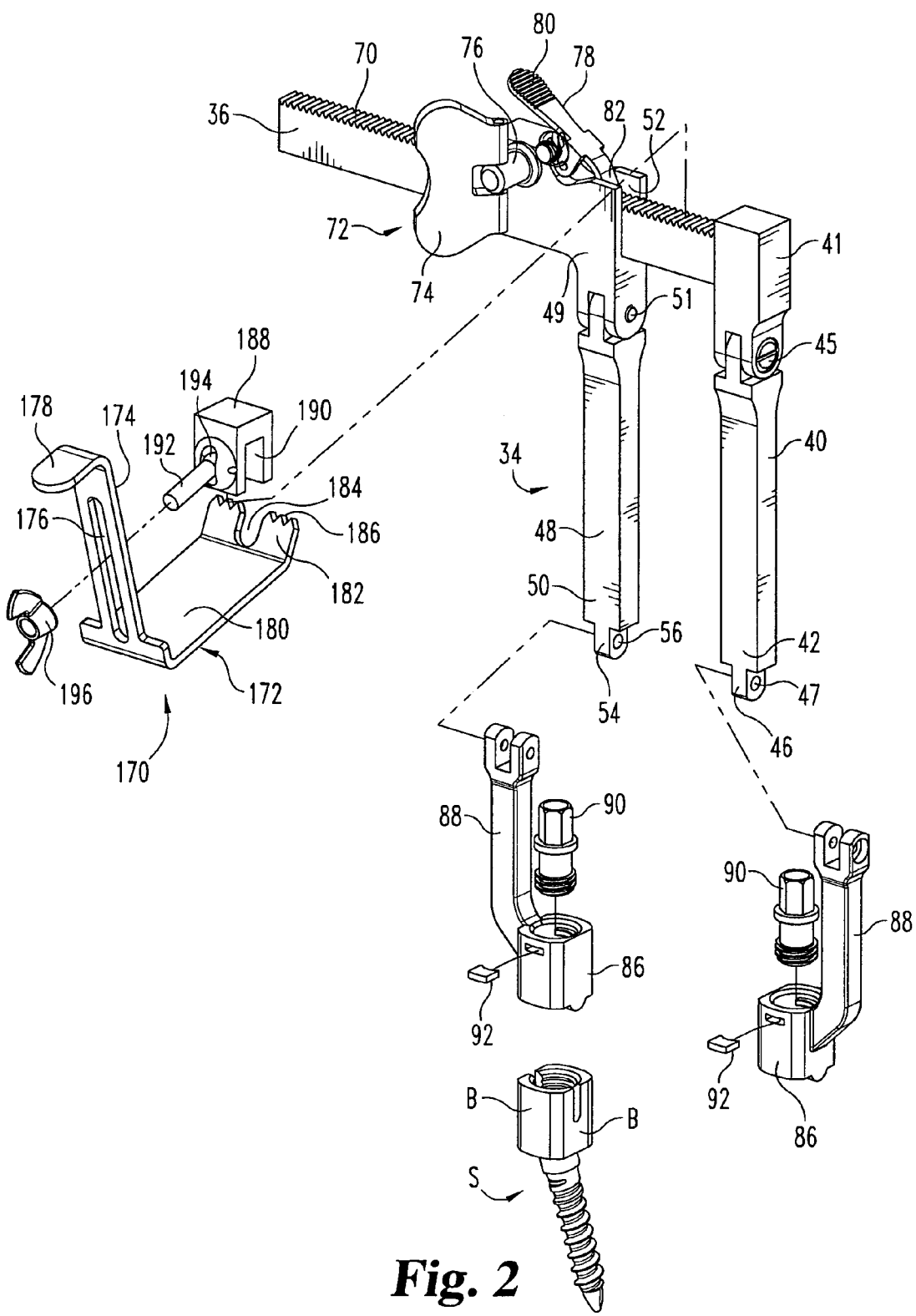
FIG. 2 is an exploded view in perspective of the embodiment shown in FIG. 1 with additional structure.
Figure 3:
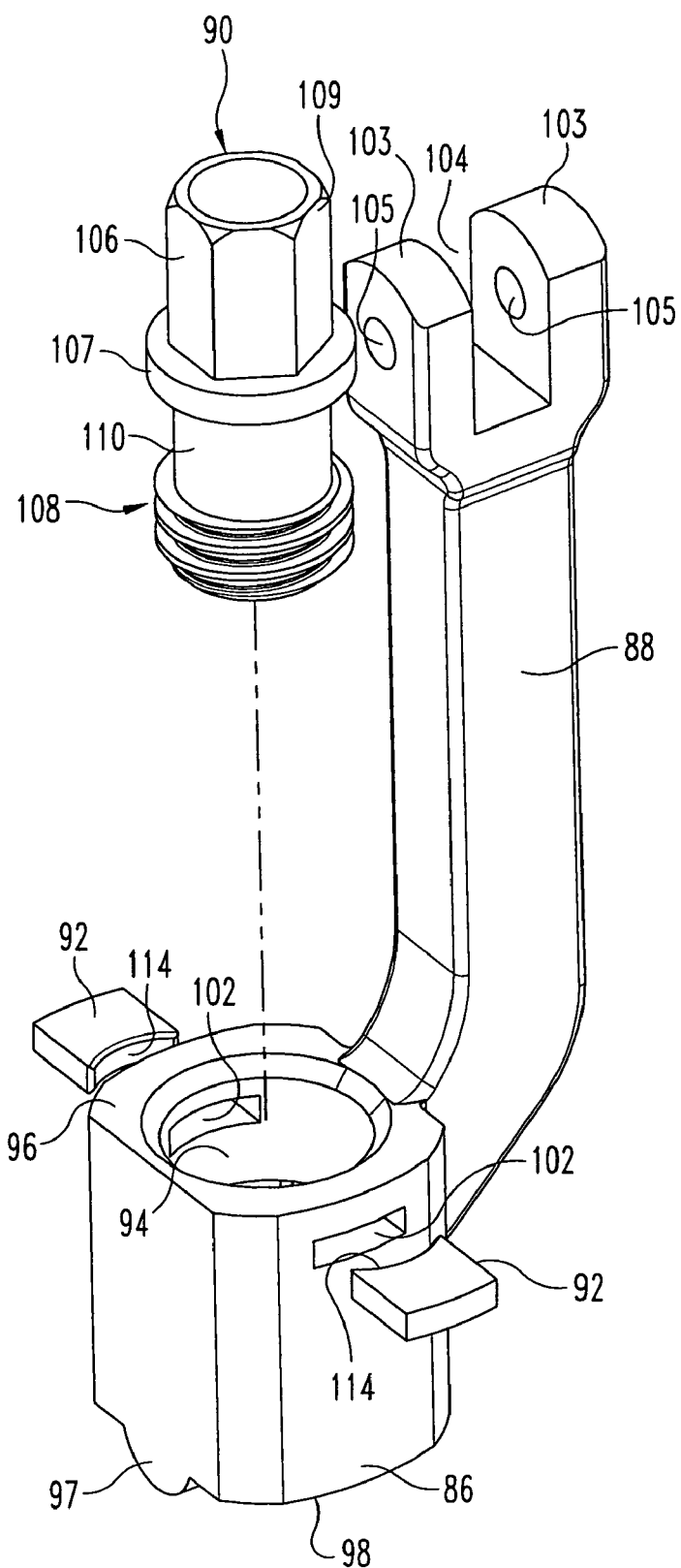
FIG. 3 is an exploded view in perspective of an aspect of the embodiment shown in FIG. 1.

As seen in the embodiment shown in FIG. 2, a retractor blade assembly 170 may be provided with an embodiment of instrument 30. Assembly 170 includes a retractor blade 172 that is substantially L-shaped in the illustrated embodiment, having a first leg 174 with a longitudinal slot 176 and an extending tab 178, and a second leg 180 substantially perpendicular to leg 174 and having an end portion 182 with a U-shaped opening 184 and a set of teeth 186. End portion 182 in a particular embodiment is at an angle with respect to leg 180. A holding piece 188 having a channel 190 and an extending shaft 192 is also provided. Channel 190 may be sized and configured so that a portion of rod 36 can fit within it and holding piece 188 can sit on rod 36. Shaft 192 is threaded and pivotable along a slot 194 in the illustrated embodiment, and is inserted through slot 176 in leg 174. A nut 196, such as a wing nut, can be tightened onto shaft 192 to secure holding piece 188 to leg 174, and to limit or prevent further pivoting of shaft 192.

Retractor blade assembly 170 can be used to retract tissue or hold it out of the way of the surgeon. The surgeon may move blade 172 up or down with respect to holding piece 188 and rod 36, and may pivot blade 172 with respect to holding piece 188 and rod 36, by loosening nut 196 and making the appropriate adjustments. Blade 172 may also be pivoted with respect to arms 32 and 34 (or arms 132 and 134) by pivoting rod 36 and ends 41 and 49 around axles 45 and 51. Blade 172 can thus be placed in a position most advantageous to the surgeon, or can be removed altogether if desired.

It has been previously noted that rod 36, with ends 41 and 49 of arms 32 and 34 (or arms 132 and 134), may be pivoted around axles 45 and 51. Such pivoting enables the surgeon to adapt instrument 30 to the surgical environment and physical needs of the case.

It will be appreciated that the parts of the embodiments shown and described may be made of biocompatible materials such as stainless steel, titanium, ceramics or hard plastics, or other known or developed biocompatible materials. Materials that can be easily sterilized and reused may be particularly useful.

In the embodiments shown and described above, tips 86 are substantially between the legs 88 of assemblies 60, or between arms 32 and 34. Other embodiments may find tips 86 to the side of or outside of legs 88 or arms 32 and 34, so that ends 41 and 49 may come closer to each other along rod 36.

Rod 36, in alternative embodiments, may be threaded rather than toothed. For example, left-hand threads may be provided on one portion of rod 36 and right-hand threads may be provided on another portion of rod 36 for purposes of distraction. In such embodiments, alternative mechanisms for controlling arm 34, including moving arm 34 relative to arm 32, can be provided, as well as a knob or other device for turning rod 36. Yet other embodiments of rod 36 may be roughened or smooth. Further, in other embodiments it may be arm 34 that is fixed and arm 32 that is movable with respect to rod 36.

While the illustrated embodiments show two arms each with a tip as disclosed, it will be seen that an instrument can be made and used in which one such arm (e.g. arm 32) is provided with a tip such as tip 86, and a different structure or mechanism is provided for connecting to a bone, implant or other object.

The U.S. patent application Ser. No. 11/118,641, entitled INSTRUMENT FOR COMPRESSION OR DISTRACTION, filed on Apr. 29, 2005, first-named inventor Alan Rezach, is incorporated herein by reference in its entirety.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. An apparatus for connecting to orthopedic implants having upper branches defining a channel, comprising:
   a first arm and a second arm, said arms being movable with respect to each other substantially in a plane;
   a pair of tips, one of said tips connected to said first arm and the other of said tips connected to said second arm, each said tip including an opening therethrough, a tab along a bottom surface of said tip that bifurcates said opening in a lower portion of said tip, said opening in a lower portion of said tip configured to accommodate the branches of an orthopedic implant so that said tab is between the branches; and
   an anchor member within said opening in an upper portion of each said tip having a head portion and a lower portion, said lower portion adapted to connect to at least one of the branches of an orthopedic implant when the branches are in said tip, so that the implant is held in said tip,
   whereby moving said arms with respect to each other moves said tips and the implants held therein with respect to each other.

2. The apparatus of claim 1, wherein said arms are connected by an elongated member.

3. The apparatus of claim 2, wherein said elongated member includes teeth, and one of said arms is connected to a pinion engaged to said teeth, whereby turning said pinion moves said arm with respect to said elongated member.

4. The apparatus of claim 3, wherein said arm not connected to said pinion is fixed with respect to said elongated member.

5. The apparatus of claim 2, wherein said elongated member is connected to said arms by axles, whereby said elongated member is pivotable with respect to said arms.

6. The apparatus of claim 1, further comprising a retractor blade connected to said elongated member, said retractor blade having a leg, said retractor blade being pivotable with respect to said elongated member and adjustable so that said leg can be at any of a number of distances from said elongated member.

7. The apparatus of claim 1, further comprising at least one retractor blade connected to at least one of said arms.

8. The apparatus of claim 1, wherein said arms each include a medial portion, and each said tip is connected to its respective medial portion via a respective axle, whereby said tip is able to pivot with respect to said medial portion.

9. The apparatus of claim 1, wherein a hole extends through said tab and communicates with said opening, said hole being large enough to pass a guide wire therethrough.

10. The apparatus of claim 1, wherein said anchor member is a screw having a threaded portion, a head portion, a collar, and a hole therethrough, said hole being at least large enough to pass a guide wire therethrough.

11. The apparatus of claim 1, wherein a tab of at least one of said tips extends from the bottom surface of said tip.

12. An apparatus for connecting to orthopedic implants having upper branches defining a channel, comprising:
   a first arm and a second arm, said arms being movable with respect to each other substantially in a plane;
   a pair of tips, one of said tips connected to said first arm and the other of said tips connected to said second arm, each said tip including an opening therethrough, a tab along a bottom surface of said tip that bifurcates said opening in a lower portion of said tip, said opening in a lower portion of said tip configured to accommodate the branches of an orthopedic implant so that said tab is between the branches;
   an anchor member within said opening in an upper portion of each said tip having a head portion and a lower portion, said lower portion adapted to connect to at least one of the branches of an orthopedic implant when the branches are in said tip, so that the implant is held in said tip,
   whereby moving said arms with respect to each other moves said tips and the implants held therein with respect to each other;
   wherein said arms each include a hollow medial portion, and each said tip is connected to a respective leg, each said leg fitting telescopically within a respective medial portion; and
   wherein each said leg includes a plurality of holes, and each said medial portion is provided with a locking arm having a protrusion, said protrusion extending into said medial portion, said protrusion sized to be able to fit at least partially into said holes, whereby said leg is adjustable with respect to said medial portion and said tip is positionable at a plurality of distances from said medial portion.

13. The apparatus of claim 12, wherein said arms each include a hollow medial portion, and each said tip is connected to a respective leg, each said leg fitting telescopically within a respective medial portion.

14. The apparatus of claim 12, wherein each said tip includes at least one side aperture that communicates with said opening, and further comprising at least one stake inserted into at least one said side aperture so that a portion of said stake extends into said opening.

15. The apparatus of claim 14, wherein said anchor member includes a collar sized so that said collar cannot pass said at least one stake.

16. The apparatus of claim 12, wherein said anchor member is a set screw.

17. The apparatus of claim 12, wherein at least one of said tips includes a pair of side apertures, and further comprising a pair of stakes each fixed in a respective one of said side apertures so that a portion of said stakes extend into said opening.

18. The apparatus of claim 17, wherein at least one of said stakes includes a concave surface, said concave surface being at least partially within said opening.

19. The apparatus of claim 12, wherein at least one of said arms includes a hollow medial portion;
   the apparatus further comprising a leg connected to at least one of said tips, said leg having a plurality of holes and configured to be inserted telescopically into said hollow medial portion; and
   a locking arm connected to said hollow medial portion, said locking arm having a protrusion that extends into said hollow medial portion and into one of said holes in said leg so that the length of said leg extending from said hollow medial portion is variable.

20. An apparatus for connecting to orthopedic implants having upper branches defining a channel, comprising:
   a first arm and a second arm, said arms being movable with respect to each other substantially in a plane;
   a pair of tips, one of said tips connected to said first arm and the other of said tips connected to said second arm, each said tip including an opening therethrough, a tab along a bottom surface of said tip that bifurcates said opening in a lower portion of said tip, said opening in a lower portion of said tip configured to accommodate the branches of an orthopedic implant so that said tab is between the branches;
   an anchor member within said opening in an upper portion of each said tip having a head portion and a lower portion, said lower portion adapted to connect to at least one of the branches of an orthopedic implant when the branches are in said tip, so that the implant is held in said tip,
   whereby moving said arms with respect to each other moves said tips and the implants held therein with respect to each other; and
   wherein each said tip includes at least one side aperture that communicates with said opening, and further comprising at least one stake inserted into at least one said side aperture so that a portion of said stake extends into said opening.

21. The apparatus of claim 20, wherein said anchor member includes a collar sized so that said collar cannot pass said at least one stake.

22. The apparatus of claim 20, wherein said arms each include a hollow medial portion, and each said tip is connected to a respective leg, each said leg fitting telescopically within a respective medial portion.

23. The apparatus of claim 20, wherein said anchor member is a set screw.

24. The apparatus of claim 20, wherein at least one of said tips includes a pair of side apertures, and further comprising a pair of stakes each fixed in a respective one of said side apertures so that a portion of said stakes extend into said opening.

25. The apparatus of claim 24, wherein at least one of said stakes includes a concave surface, said concave surface being at least partially within said opening.

26. The apparatus of claim 20, wherein at least one of said arms includes a hollow medial portion;
   the apparatus further comprising a leg connected to at least one of said tips, said leg having a plurality of holes and configured to be inserted telescopically into said hollow medial portion; and
   a locking arm connected to said hollow medial portion, said locking arm having a protrusion that extends into said hollow medial portion and into one of said holes in said leg so that the length of said leg extending from said hollow medial portion is variable.

27. An apparatus for connecting to orthopedic implants having upper branches defining a channel, comprising:
   an arm;
   an elongated member connected to said arm, said arm being movable along the length of said elongated member;
   a tip connected to said arm, said tip including an opening therethrough, a tab along a bottom surface of said tip that bifurcates said opening in a lower portion of said tip, said opening in a lower portion of said tip configured to accommodate the branches of an orthopedic implant so that said tab is between the branches; and
   an anchor member within said opening in said tip, said anchor member having a head portion and a lower portion, said lower portion adapted to connect to at least one of the branches of an orthopedic implant when the branches are in said tip, so that the implant is held in said tip,
   whereby moving said arm with respect to said elongated member moves said tip and the implant held therein with respect to said elongated member.

28. The apparatus of claim 27, wherein said arm includes a tongue having a hole therethrough;
   the apparatus further comprising a leg having a first end and a second end, said first end connected to said tip, said second end having a pair of prongs defining a slot, each said prong having hole therethrough;
   said tongue being inserted into said slot so that said hole in said tongue and said holes in said prongs are substantially collinear; and
   further comprising an axle inserted through said hole in said tongue and said holes in said prongs,
   whereby said leg and said tip can be pivoted with respect to said arm.

29. The apparatus of claim 28, wherein at least one of said prong holes includes internal threads, and said axle is at least partially threaded, so that said axle can be threaded into said at least one threaded prong hole.

30. The apparatus of claim 27, wherein said tab has a hole therethrough, said hole being at least large enough to allow a guide wire to pass through.

31. The apparatus of claim 27 wherein said anchor member has a collar for retaining said anchor member within said opening.

32. The apparatus of claim 27 wherein said anchor member has a hole sized at least large enough to pass a guide wire therethrough.

33. The apparatus of claim 27 wherein said elongated member is connected to said arm via an axle.

34. The apparatus of claim 33, wherein said axle is substantially perpendicular to said arm.

35. The apparatus of claim 33, wherein said axle is substantially parallel to said elongated member.

36. The apparatus of claim 27, wherein said tab of said tip extends from the bottom surface of said tip.

37. An apparatus for connecting to orthopedic implants having upper branches defining a channel, comprising:
   an arm;
   an elongated member connected to said arm, said arm being movable along the length of said elongated member;
   a tip connected to said arm, said tip including an opening therethrough, a tab along a bottom surface of said tip that bifurcates said opening in a lower portion of said tip, said opening in a lower portion of said tip configured to accommodate the branches of an orthopedic implant so that said tab is between the branches;
   an anchor member within said opening in said tip, said anchor member having a head portion and a lower portion, said lower portion adapted to connect to at least one of the branches of an orthopedic implant when the branches are in said tip, so that the implant is held in said tip,
   whereby moving said arm with respect to said elongated member moves said tip and the implant held therein with respect to said elongated member; and wherein said tip includes a pair of side apertures, and further comprising a pair of stakes each fixed in a respective one of said side apertures so that a portion of said stakes extend into said opening.

38. The apparatus of claim 37, wherein at least one of said stakes includes a concave surface, said concave surface being at least partially within said opening.

39. The apparatus of claim 37, wherein said arm includes a hollow medial portion, and said tip is connected to a leg, said leg fitting telescopically within said hollow medial portion.

40. The apparatus of claim 37, wherein said arm includes a hollow medial portion;
the apparatus further comprising a leg connected to said tip, said leg having a plurality of holes and configured to be inserted telescopically into said hollow medial portion; and
a locking arm connected to said medial portion, said locking arm having a protrusion that extends into said medial portion and into one of said holes in said leg so that the length of said leg extending from said medial portion is variable.

41. An apparatus for connecting to orthopedic implants having upper branches defining a channel, comprising:
an arm;
an elongated member connected to said arm, said arm being movable along the length of said elongated member;
a tip connected to said arm, said tip including an opening therethrough, a tab along a bottom surface of said tip that bifurcates said opening in a lower portion of said tip, said opening in a lower portion of said tip configured to accommodate the branches of an orthopedic implant so that said tab is between the branches;
an anchor member within said opening in said tip, said anchor member having a head portion and a lower portion, said lower portion adapted to connect to at least one of the branches of an orthopedic implant when the branches are in said tip, so that the implant is held in said tip,
whereby moving said arm with respect to said elongated member moves said tip and the implant held therein with respect to said elongated member;
wherein said arm includes a hollow medial portion;
the apparatus further comprising a leg connected to said tip, said leg having a plurality of holes and configured to be inserted telescopically into said hollow medial portion; and
a locking arm connected to said medial portion, said locking arm having a protrusion that extends into said medial portion and into one of said holes in said leg so that the length of said leg extending from said medial portion is variable.

42. An apparatus for connecting to orthopedic implants having upper branches defining a channel, comprising:
a first arm and a second arm, said arms being movable with respect to each other substantially in a plane;
a pair of tips, one of said tips connected to said first arm and the other of said tips connected to said second arm, each said tip including an opening therethrough, a tab along a bottom surface of said tip that bifurcates said opening in a lower portion of said tip, said opening in a lower portion of said tip configured to accommodate the branches of an orthopedic implant so that said tab is between the branches; and
an anchor member within said opening in an upper portion of each said tip having a head portion and a lower portion, said lower portion adapted to connect to at least one of the branches of an orthopedic implant when the branches are in said tip, so that the implant is held in said tip,
whereby moving said arms with respect to each other moves said tips and the implants held therein with respect to each other, and wherein at least one of said tips is offset from one of said arms in a direction substantially toward another of said tips.

43. An apparatus for connecting to orthopedic implants having upper branches defining a channel, comprising:
a first arm and a second arm, said arms being movable with respect to each other substantially in a plane;
a pair of tips, one of said tips connected to said first arm and the other of said tips connected to said second arm, each said tip including an opening therethrough, a tab along a bottom surface of said tip that bifurcates said opening in a lower portion of said tip, said opening in a lower portion of said tip configured to accommodate the branches of an orthopedic implant so that said tab is between the branches; and
an anchor member within said opening in an upper portion of each said tip having a head portion and a lower portion, said lower portion adapted to connect to at least one of the branches of an orthopedic implant when the branches are in said tip, so that the implant is held in said tip,
whereby moving said arms with respect to each other moves said tips and the implants held therein with respect to each other, and wherein said tips are offset from their respective arms in a direction substantially toward each other.

44. An apparatus for connecting to orthopedic implants having upper branches defining a channel, comprising:
an arm;
an elongated member connected to said arm, said arm being movable along the length of said elongated member;
a tip connected to said arm, said tip including an opening therethrough, a tab along a bottom surface of said tip that bifurcates said opening in a lower portion of said tip, said opening in a lower portion of said tip configured to accommodate the branches of an orthopedic implant so that said tab is between the branches; and
an anchor member within said opening in said tip, said anchor member having a head portion and a lower portion, said lower portion adapted to connect to at least one of the branches of an orthopedic implant when the branches are in said tip, so that the implant is held in said tip,
whereby moving said arm with respect to said elongated member moves said tip and the implant held therein with respect to said elongated member, and wherein said tip is offset from said arm in a direction substantially parallel to said elongated member.

45. An apparatus for connecting to orthopedic implants having upper branches defining a channel, comprising:
a first arm and a second arm, said arms being movable with respect to each other substantially in a plane;
a pair of tips, one of said tips connected to said first arm and the other of said tips connected to said second arm, each said tip including an opening therethrough, a tab along a bottom surface of said tip that bifurcates said opening in a lower portion of said tip, said opening in a lower portion of said tip configured to accommodate the branches of an orthopedic implant so that said tab is between the branches; and an anchor member within said opening in an upper portion of each said tip having a head portion and a lower portion, said lower portion adapted to connect to at least one of the branches of an orthopedic implant when the branches are in said tip, so that the implant is held in said tip, whereby moving said arms with respect to each other moves said tips and the implants held therein with respect to each other, and wherein said arms each include a hollow medial portion, and each said tip is connected to a respective leg, each said leg fitting telescopically within a respective medial portion.

* * * * *

UNITED STATES PATENT AND TRADEMARK OFFICE
CERTIFICATE OF CORRECTION

PATENT NO. : 7,618,424 B2 Page 1 of 1
APPLICATION NO. : 11/118513
DATED : November 17, 2009
INVENTOR(S) : Wilcox et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 503 days.

Signed and Sealed this

Twenty-sixth Day of October, 2010

David J. Kappos
*Director of the United States Patent and Trademark Office*